United States Patent [19]
Augustine et al.

[11] Patent Number: 6,022,823
[45] Date of Patent: Feb. 8, 2000

[54] PROCESS FOR THE PRODUCTION OF SUPPORTED PALLADIUM-GOLD CATALYSTS

[75] Inventors: Steven M. Augustine, Mason; David W. Smith, Cincinnati; Ronnie M. Hanes, Loveland; Michael D. Evans, Cinncinnati, all of Ohio

[73] Assignee: Millennium Petrochemicals, Inc., Cincinnati, Ohio

[21] Appl. No.: 08/741,543

[22] Filed: Oct. 31, 1996

Related U.S. Application Data

[60] Provisional application No. 60/019,811, Jun. 12, 1996, and provisional application No. 60/011,586, Nov. 7, 1995.

[51] Int. Cl.[7] .............................. B01J 21/08; B01J 23/58
[52] U.S. Cl. ........................................ 502/243; 502/330
[58] Field of Search ..................... 502/330, 167, 502/174, 200, 328, 243; 252/430

[56] References Cited

U.S. PATENT DOCUMENTS

| | | | |
|---|---|---|---|
| 5,505,921 | 4/1996 | Lückoff et al. | 423/584 |
| 5,637,548 | 6/1997 | Ito et al. | 502/330 |
| 5,674,800 | 10/1997 | Abel et al. | 502/330 |
| 5,691,267 | 11/1997 | Nicolau et al. | 502/330 |
| 5,693,586 | 12/1997 | Nicolau et al. | 502/330 |

FOREIGN PATENT DOCUMENTS

| | | | |
|---|---|---|---|
| 1269113 | 5/1968 | Germany | 423/628 |
| 60-171271 | 9/1985 | Japan | 501/98.4 |

*Primary Examiner*—Wayne Langel
*Attorney, Agent, or Firm*—Wood, Herron & Evans L.L.P.

[57] ABSTRACT

An improved process for producing high activity and high selectivity supported palladium-gold catalysts is provided. The process involves calcining the support impregnated with a palladium salt and gold salt in a non-reducing atmosphere and at a temperature ranging from 100° C. to 600° C. prior to reducing the metals. Catalysts of the invention are useful for the production of vinyl acetate in the vapor phase by reaction of ethylene, acetic acid and oxygen.

29 Claims, 3 Drawing Sheets

PROCESS FOR THE PRODUCTION OF SUPPORTED PALLADIUM-GOLD CATALYSTS

CROSS-REFERENCE TO RELATED APPLICATIONS

This application claims the benefit of U.S. Provisional application Ser. No. 60/011,586 filed Nov. 7, 1995 and U.S. Provisional application Ser. No. 60/019,811 filed Jun. 12, 1996.

FIELD OF THE INVENTION

The present invention relates to an improved process for the preparation of supported palladium-gold catalysts used for the vapor phase reaction of ethylene, acetic acid and oxygen to produce vinyl acetate. More specifically, the process entails impregnating an inert support with palladium and gold salts and calcining the impregnated support before the palladium and gold are reduced to their metallic states.

BACKGROUND OF THE INVENTION

Processes for producing vinyl acetate by the vapor phase reaction of ethylene, acetic acid and oxygen using supported catalysts containing metallic palladium, metallic gold and an alkali metal acetate are known and disclosed in U.S. Pat. Nos. 3,743,607 and 3,775,342.

Various procedures are used to prepare the supported palladium-gold catalysts employed for these processes. All of the procedures generally include a reduction step. Since the metals are typically deposited on the support from aqueous metal salt solutions, they must subsequently be reduced to the corresponding metallic state by treating the support having the metal salts deposited thereon with a reducing agent, such as ethylene, propylene, isobutylene, hydrazine, hydrogen, methanol, formaldehyde, formic acid and salts, and the like. After the reduction, the support having substantially all of the palladium and gold present in the metallic form is activated by impregnating with an alkali metal acetate, such as sodium or potassium acetate.

In several instances, an oxidation step is also included in the catalyst preparation procedure. In U.S. Pat. No. 5,194,417, for example, after substantially all of the palladium and gold have been reduced to the metal, the "virgin catalyst" is oxidized or at least partially oxidized by contacting with an oxidizing agent, preferably an oxygen-containing gas, and then after removal of the oxidizing agent contacted with a reducing agent. By such treatment of "virgin catalyst," improvements in selectivity and yield are achieved.

Another process which, in one embodiment, includes both oxidation and reduction steps in the preparation of a palladium-gold supported catalyst is disclosed in U.S. Pat. No. 4,087,622. In this process, prior to deposition of the major proportion of the palladium and gold, a small amount of metal salt is deposited on the support, converted to the corresponding metal oxide and then subsequently reduced to the metal. This sequential oxidation and reduction of metal salts to achieve predeposition of small amounts of metal on the support before deposition of the major portion of palladium and gold is distinguished from the present invention where all of the metal salt is deposited onto the support and the impregnated support heated in a non-reducing atmosphere before reducing.

U.S. Pat. No. 3,917,676 discloses palladium-lead catalysts for the reaction of propylene and acetic acid with oxygen to produce allylacetate. In one embodiment, after deposition of the metal salts and drying, the palladium-lead catalyst is sintered in air at 250° C. for 5 hours and then subjected to hydrogen reduction at 200° C. for 5 hours.

SUMMARY OF THE INVENTION

It has now been discovered that high selectivity and high activity supported palladium-gold catalysts are produced when, during the catalyst preparation, the impregnated support is calcined before reducing the metals. The catalysts produced by the process of the invention are useful for the production of vinyl acetate by the vapor phase reaction of acetic acid, ethylene and oxygen. More specifically, the process of the invention is directed to an improved process for the preparation of supported palladium-gold catalysts wherein an inert support is impregnated with palladium and gold salts and, prior to the reduction, the impregnated support is calcined by heating in a non-reducing atmosphere at a temperature from about 100° C. to about 600° C. to bring about at least partial decomposition of the palladium and gold salts. Catalysts produced by the improved process of the invention contain from 0.1 to 3 weight percent palladium, 0.1 to 3 weight percent gold and have a weight ratio of palladium to gold from 5:1 to 1:3. Inert supports used in the process have pore volumes from 0.1 to 0.75 cc/g and surface areas from 0.5 to 500 $m^2/g$ and preferably are alumina, silica, silica-alumina and titania.

The calcination is conducted in a non-reducing atmosphere which typically is an inert or oxidizing gas such as helium, nitrogen, argon, neon, nitrogen oxides, oxygen or air. Atmospheres of nitrogen, oxygen, air or mixtures thereof are most commonly used for the calcining step. Reduction can be accomplished utilizing conventional procedures and reducing agents which can include ammonia, carbon monoxide, hydrogen, hydrocarbons, olefins, aldehydes, alcohols, hydrazine, primary amines, carboxylic acids, carboxylic acid salts and carboxylic acid esters. While the reduction can be carried out at temperatures from ambient up to 550° C., it is preferred to reduce the palladium and gold at a temperature from 100 to 550° C. Highly useful reducing agents include hydrogen, ethylene, propylene, alkaline hydrazine and alkaline formaldehyde with ethylene and hydrogen being preferred.

Using the process of the invention, it is possible to tailor catalysts covering the full spectrum of selectivity and activity by varying conditions during the calcination and reduction. In one highly useful embodiment of the invention to produce high selectivity catalysts, the impregnated support is calcined in a non-reducing atmosphere at a temperature from about 350° C. up to about 600° C. prior to reduction which is preferably carried out using hydrogen and at a temperature from 350 to 525° C. It is even more preferable to conduct the calcination at 450 to 550° C. and reduce at a temperature from 450 to 500° C. In another highly useful embodiment which favors production of high activity catalysts, the impregnated support is calcined at a temperature from 100 to 350° C. and, more preferably, in the range 150° C. to 275° C. before reducing the palladium and gold. Preferably, in this procedure the reduction is carried out using hydrogen while gradually increasing the temperature up to a maximum of about 525° C.

DETAILED DESCRIPTION OF THE INVENTION

Improved supported bimetallic catalysts useful for the preparation of vinyl-esters, particularly vinyl acetate (VA) by the vapor phase reaction of ethylene, acetic acid and oxygen, are provided. The catalysts of the invention having improved activity and selectivity comprise palladium (Pd) and gold (Au) impregnated on an inert support. In another aspect of the invention there is provided a novel procedure for preparing supported Pd—Au catalysts wherein the support impregnated with the palladium and gold salts is calcined by heating in a non-reducing atmosphere to decompose all or a portion of the palladium and gold salts before reducing to the corresponding metals. In one highly useful embodiment the palladium and gold salts are reduced by heating the impregnated support in the presence of hydrogen.

The improved catalysts of the invention will have substantially higher selectivity and/or increased activity depending on the conditions employed for the calcining and reduction. In one procedure designed to produce catalysts having optimal selectivity, the calcination is carried out at relatively high temperatures, i.e., greater than about 350° C. The supported Pd—Au catalysts produced in this manner exhibit high selectivity and are useful in processes for the production of vinyl acetate where oxygen conversion is pushed to nearly complete consumption. In another embodiment, high activity catalysts, i.e., having high space-time-yields, are produced. Such catalysts are useful in processes where the oxygen conversion is not a limiting factor but rather the process is concerned with optimal productivity of VA. To obtain high activity catalysts, the temperature employed during the calcination step should generally not exceed about 350° C.

Any of the conventional inert support materials heretofore used for the preparation of palladium-gold catalysts for processes of this type can be used for the present invention. These can include for example, alumina, silica, silica-alumina, silica gel, silicic acid, silicates, titania, pumice, diatomaceous earth, silicon carbide and the like. In general, the inert supports, sometimes also referred to as the catalyst carrier or porous carried will have pore volumes from 0.1 cc/g to 0.75 cc/g and surface areas from 0.5 $m^2$/g to 500 $m^2$/g. Most preferably, pore volumes will range from 0.2 cc/g to 0.65 cc/g and surface areas will range from 1 $m^2$/g to 200 $m^2$/g. In a highly useful embodiment of the invention, the surface area of the support is from 2 to 50 $m^2$/g and the support is alumina or titania. Alumina supported Pd—Au catalysts are a particularly useful embodiment of the invention and, it is even more preferred if the alumina carrier has a high alpha-alumina content—typically, greater than 95 percent. In another highly useful embodiment where the support is silica or silica-alumina, the surface area of the support is 30 to 200 $m^2$/g. While the catalyst supports are most commonly in the form of particles, spheres or pellets, other shapes such as rods or cylinders and loose packing configurations, e.g., stars and rings, can be used.

Procedures to impregnate the inert support are generally known and conventional. Typically the porous support material is simultaneously or, as is more often the case, successively treated with an aqueous solution of palladium and gold salts and an aqueous solution of an alkali metal compound which react on the support to form palladium and gold salts. The concentration of the solutions and the amount of each solution used is governed by the concentration of palladium and gold desired in the final catalyst product. Water is then removed leaving the palladium and gold salts deposited on the support. The dried support having the palladium and gold salts deposited thereon is then subjected to calcination and reduction in accordance with the process of the invention and as will be described in more detail to follow.

In the practice of the invention, deposition of the noble metal salts onto alumina or titania is generally accomplished by first treating the support with an aqueous solution of an alkali metal compound such as an alkali metal hydroxide, alkali metal carbonate, alkali metal bicarbonate, alkali metal metasilicate and the like. The volume of aqueous alkali solution employed is sufficient to fill from about 25 to 95 percent of the absorptive capacity of the support. More typically, 50 to 90 percent of the support pore volume is filled. In a highly useful embodiment of the invention, 70 to 85 percent of the absorptive capacity of the support is filled with an aqueous solution of sodium carbonate. For the purpose of this invention, the pore volume of the support is considered to be its absorptive capacity.

The alumina or titania support which has been treated with the aqueous solution containing the alkali metal compound is then contacted with a second aqueous solution containing dissolved salts of palladium and gold. Representative palladium and gold salts which can be used in the preparation of the second aqueous solution include palladium chloride, sodium chloropalladite, palladium nitrate, palladium sulfate, auric chloride, tetrachloroauric acid, sodium tetrachloroaurate, and the like. Solutions of tetrachloroauric acid and palladium chloride or sodium chloropalladite are most commonly used in view of their high water solubility and ready availability.

For another preferred embodiment of the invention where the support is silica or silica-alumina, impregnation with the palladium and gold solutions is carried out before treatment with the aqueous solution of the alkali metal compound. In this procedure the absorptive capacity of the support is essentially completely filled with the aqueous solution of palladium and gold salts. Typically, this is accomplished by dropping the solution onto the support until incipient wetness is achieved. The support impregnated with the palladium and gold salts is then contacted with a molar excess, based on the reaction stoichiometry, of the alkali metal compound. This is conveniently accomplished by immersing the impregnated support in the aqueous solution of the alkali metal compound. When silica or silica-alumina supports are treated in this manner, the alkali metal compound is preferably an alkali metal carbonate.

Whereas preparations of the catalysts of the invention to this point in the process are conducted in accordance with conventional procedures, in a deviation from the prior art processes, the impregnated supports are calcined, i.e., heated at an elevated temperature but below the melting point in a non-reducing atmosphere, before proceeding with the reduction. The calcining operation is an essential feature of the process. During calcination the palladium and gold salts impregnated on the support are decomposed. Generally a portion of the palladium and gold salts will be decomposed by this treatment—the mode and extent of decomposition depending on the calcination conditions. Even though the calcination is carried out in a non-reducing atmosphere, both metals but primarily the gold can also undergo autoreduction due to their chemical potential. Some autoreduction occurs even when the calcination is carried out at the lower end of the temperature range.

The calcination is carried out at a temperature in the range of about 100° C. to about 600° C. Non-reducing gases used for the calcination are inert or oxidizing gases such as helium, nitrogen, argon, neon, nitrogen oxides, oxygen, air, carbon dioxide and the like. Mixtures of the aforementioned gases may also be used. In a highly useful embodiment of the invention, the calcination is carried out in an atmosphere of nitrogen, oxygen or air or mixtures thereof Calcination times will vary but most generally are between about 1 and 5 hours.

It is a highly desirable aspect of the invention that the catalyst characteristics can be altered by varying the conditions employed in the calcination step. Catalysts covering the full spectrum of selectivity and activity can be produced in this manner. For example, by calcining the impregnated support at a temperature range from about 100° C. up to about 350° C., high activity catalysts are produced. On the other hand, when the impregnated support is calcined, i.e., heated, in a non-reducing atmosphere, at a temperature above about 350° C., high selectivity catalysts are obtained. Thus, with the process of the invention, it is possible to produce supported Pd—Au catalysts having optimal activity, optimal selectivity or a balance of activity and selectivity somewhere between the optimum values. This is significant since plant designs and equipment vary and require the use of different operating conditions and catalysts to achieve maximum productivity. With the present process, catalysts can be designed to optimize performance for specific production conditions.

The degree of decomposition of the Pd and Au salts depends on the temperature used and length of time the impregnated catalyst is calcined and can be followed by monitoring volatile decomposition products. For example, when the support is impregnated with Pd and Au carbonates, the amount of carbon dioxide ($CO_2$) evolved can be measured. The ability to follow the decomposition makes it possible to control the type of catalyst which is produced.

Following the calcination step, the resulting product is reduced to convert the palladium and gold salts to the corresponding metals. In general, any known procedure using conventional reducing agents such as ammonia, carbon monoxide, hydrogen, hydrocarbons, olefins, aldehydes, alcohols, hydrazine, primary amines, carboxylic acids, carboxylic acid salts and carboxylic acid esters can be used. Hydrogen, ethylene, propylene, alkaline hydrazine and alkaline formaldehyde are highly useful reducing agents and ethylene and hydrogen are particularly preferred. Temperatures employed for the reduction can range from ambient up to about 550° C.

Since the procedure used to reduce the metals influences the characteristics of the final catalyst, conditions employed for the reduction will be varied depending on whether high activity, high selectivity or some balance of these properties is desired. In one highly useful embodiment of the invention, the reduction is carried out at a temperature from about 100° C. up to about 550° C. Even more preferably, the reduction at elevated temperature is carried out using hydrogen as the reducing agent. While pure hydrogen may be used, it is more common to utilize a mixture of hydrogen and an inert gas such as nitrogen, helium, argon, neon or the like. These mixtures generally contain up to about 50 percent hydrogen and, more typically, are comprised of about 5 to 25 percent hydrogen and 75 to 95 percent inert gas. Reduction times will typically vary from 1 to 5 hours.

Palladium-gold supported catalysts which exhibit a high degree of selectivity for the production of vinyl acetate, based on oxygen, can be produced by judicious selection of conditions used for the calcination and reduction. In one procedure, the impregnated support which is preferably alumina or titania, is heated in a non-reducing atmosphere at a temperature from about 350° C. up to about 600° C. to decompose 70 percent or more of the Pd and Au salts and subsequently reduced in hydrogen at a temperature from about 100° C. up to about 550° C. to convert substantially all of the Pd and Au to the metals. In an even more preferred process, the impregnated support is calcined from about 400° C. up to about 550° C. to decompose 85 percent or more of the salts and then reduced from about 350° C. up to about 525° C. It is even more preferred if, after calcining, the resulting product is reduced in hydrogen at a temperature from about 450° C. up to about 500° C. The supported Pd—Au catalysts produced in this manner exhibit superior selectivity and are highly useful in reactions where oxygen is the limiting reagent, i.e., where oxygen conversion is typically 97 percent or greater. In these situations, the inherent activity of the catalyst is not fully utilized since oxygen is limited and it is therefore highly advantageous to utilize as much of the oxygen as possible for the production of the desired product, i.e., vinyl acetate. Highly selective supported Pd—Au catalysts having segregated palladium-enriched and gold-enriched crystallite phases appearing as two distinct peaks in the x-ray diffraction pattern between the 2-Theta angles of 38° and 41° can be produced. The palladium-enriched and gold-enriched crystallites have d-space separations of the Miller 111 index plane in the range from about 2.246 Å to about 2.257 Å and about 2.343 Å to about 2.355 Å, respectively.

In another embodiment of the invention, alumina, titania, silica or silica-alumina supported Pd—Au catalysts having high activity are produced. High activity catalysts are advantageous in processes where most of the oxygen is not consumed but rather is present in excess so as to optimize space-time-yield. Processes of this type are commonly used in commercial operations where high productivity of vinyl acetate is desired.

To obtain catalysts having optimum activity, the impregnated support is calcined in the non-reducing gas at a temperature below about 350° C. and, preferably in the range, 150° C. to 275° C. Metal salt decomposition under these conditions typically ranges from 10 to 70 percent and, more commonly, from 30 to 60 percent. At the conclusion of the calcining operation the product is then reduced in accordance with the previously described procedure. While the reduction may be carried out over the standard temperature range, i.e., 100° C. to 550° C., best results are achieved by reducing at a temperature from about 150° C. to about 525° C. It is even more advantageous if during the reduction, the temperature is gradually increased from the temperature used for the calcining up to the maximum temperature used for the reduction—generally 475° C. to 525° C. The rate at which the temperature is increased can be from about 0.1° C. per minute up to about 25° C. per minute but most generally will be from 1° C. per minute to 15° C. per minute. This aspect of the invention is conveniently accomplished by purging the system of non-reducing gas at the completion of the calcining operation while maintaining the temperature and then introducing hydrogen or the hydrogen/inert gas mixture while increasing the temperature at the desired rate up to the maximum temperature desired for the reduction. The temperature is then maintained for the remainder of the reduction period. In a particularly useful embodiment of the invention for the production of high activity catalysts, the calcination is carried out at 175° C. to 250° C. and the resulting calcined product then reduced while the temperature is "ramped up" from the calcination temperature to about 500° C. at a rate of from 5° C. to 15° C. per minute. High activity supported palladium-gold catalysts produced in accordance with the foregoing calcination and reduction procedure have enriched palladium and gold crystallite phases which appear as two distinct peaks in the x-ray diffraction patterns between the 2-Theta angles of 38° and 41°. The palladium and gold crystallites have d-space separations of the Miller 111 Index plane in the range from about 2.259 Å to about 2.273 Å and from 2.343 Å to about 2.355 Å, respectively.

Catalysts produced by the process of the invention wherein the impregnated support is calcined before reducing the metals have palladium contents from about 0.1 weight percent up to about 3 weight percent and gold contents from about 0.1 weight percent up to about 3 weight percent. More preferably, the catalysts contain 0.5 to 1.5 weight percent palladium and 0.25 to 0.75 weight percent gold. The weight ratio of palladium to gold generally ranges from about 5:1 to about 1:3 and, more preferably, is in the range 2.5:1 to 1:1.5. The weight percentages and ratios of Pd and Au are applicable without regard to the catalyst characteristics, i.e., whether the catalyst exhibits high activity, high selectivity or a balance of selectivity and activity.

In accordance with conventional practice with supported Pd—Au catalysts for the vapor phase reaction of ethylene, acetic acid and oxygen to produce vinyl acetate, catalysts obtained from the process of the invention are activated by treating with an alkali metal carboxylate and/or alkali metal hydroxide prior to use. Conventional alkali metal carboxylates such as the sodium, potassium, lithium and cesium salts of $C_{2-4}$ aliphatic carboxylic acids are employed for this purpose. The amount of activating agent will typically range from 1 to 15 percent. Sodium and potassium acetate are most commonly used to activate the catalysts, optionally, with the corresponding alkali metal hydroxide. Activation is accomplished by applying a solution containing the alkali metal carboxylate to the reduced catalyst and thereafter drying to remove the water. It is also possible to apply the alkali metal carboxylate by reacting an alkali metal compound, such as a hydroxide, carbonate or borate of the alkali metal, with the carboxylic acid in the presence of the supported Pd—Au catalyst.

In a preferred embodiment of the invention where high selectivity or high activity Pd—Au catalysts supported on alumina or titania are prepared, the catalysts are activated by treating with an aqueous solution containing 1 to 15 weight percent and, more preferably, 2.5 to 10 weight percent potassium acetate and up to 5 weight percent potassium hydroxide. More preferably, when potassium hydroxide is employed in the activation step, it is used in an amount from 0.1 to 3 weight percent. In another preferred embodiment where high activity catalysts supported on silica or silica-alumina are prepared, activation is achieved by treating with an aqueous solution containing 1 to 4 percent potassium acetate.

Catalysts prepared in accordance with the present invention are advantageously employed for the production of vinyl acetate by the vapor phase reaction of ethylene, acetic acid and oxygen. The catalysts are highly effective under a variety of operating conditions as has been previously discussed and exhibit long life before requiring reactivation. With the process of the invention it is possible to tailor catalysts having the desired characteristics, i.e., selectivity and activity, so that maximum productivity can be achieved under a given set of operating conditions.

The following examples illustrate the various embodiments of the invention more fully and are provided to enable those skilled in the art to practice the invention. These examples are not, however, intended as a limitation on the scope of the invention as numerous variations will be apparent therefrom. In the examples all parts and percentages are on a weight basis unless otherwise indicated.

Weight percentages of palladium and gold were determined by inductively coupled plasma atomic emission spectroscopy (ICP). X-ray diffraction data for the supported Pd—Au catalysts were collected using a powder diffractometer with a copper source and an nickel filter. Catalyst samples were ground to an average particle size of less than 120 microns and a conventional X-ray sample holder was employed. The x-ray wavelength used was 1.54056 Å which corresponds to the copper K-alpha emission. Data were collected and profiles plotted between the 2-Theta angles of 36° and 50° in 0.02° increments with a counting period of 3 seconds at each increment. The resulting diffraction pattern was corrected relative to known diffraction lines of the inert support and the 2-Theta diffraction angle data converted to d-spacing of Miller index planes using Bragg's law. When silica is employed as the support, ground-alumina is added to serve as an internal standard.

The catalyst pellets were evaluated for vinyl acetate production using a packed bed plug flow tubular (nominal 1 inch O.D. stainless steel) reactor. The bed volume was 30 ml which produced a catalyst depth of approximately 3 inches. Pressure, temperature, feed rates and space velocity were varied depending on whether the primary focus was on catalyst selectivity or catalyst activity.

In the process designed to evaluate high selectivity catalysts, referred to herein as Procedure A, oxygen is the limiting reagent and conditions are employed so that $O_2$ conversion is pushed to near complete consumption. Feed rates (mol/hr) used for Procedure A were as follows:

| | |
|---|---|
| Ethylene | 0.403 |
| Acetic Acid | 0.115 |
| Oxygen | 0.0444 |
| Water | 0.0202 |
| Nitrogen | 0.0190 |

Since under conditions of essentially complete oxygen conversion the inherent activity of the catalyst is not fully utilized, the catalysts of the invention were also evaluated under conditions to optimize space-time-yield. These processes, referred to herein as Procedure B, were conducted using the following feed rates (mol/hr):

| | |
|---|---|
| Ethylene | 1.37 |
| Acetic Acid | 0.325 |
| Oxygen | 0.125 |
| Water | 0.0570 |
| Nitrogen | 0.0532 |

Catalyst activity was also determined on a micro scale. These scaled-down reactions provide a rapid and reliable means of determining the rate of reaction using a small amount of catalyst. Reaction rates, which are an indication of catalyst activity, are reported as micromols of vinyl acetate produced per gram of catalyst per second ($\mu$moles/g cat.-sec). The micro reactor had a 3/8 inch glass reactor tube with a catalyst volume of approximately 0.4 ml. 0.5 grams ground catalyst was used for these reactions which were carried out at 1 atmosphere pressure (14.7 psia) and 140° C. Feed rates (mol/hr) and space velocity (/hr) used for the micro reactions were as follows:

| | |
|---|---|
| Ethylene | 0.225 |
| Acetic Acid | 0.018 |
| Oxygen | 0.025 |
| Space Velocity | 1,600 |

EXAMPLE 1

A series of Pd—Au supported catalysts having improved selectivity were prepared in accordance with the following general procedure. Three hundred (300) grams alumina (5/16" pellet; 98% alpha alumina; pore volume 0.23 mug; surface area approximately 4 m$^2$/g; crush strength 25–45 lbs.) were sprayed with a volume of 2.33 N Na$_2$CO$_3$ aqueous solution calculated to fill approximately 75% of the pore volume and then with a solution of 3.05 g HAuCl$_4$, 6.33 g PdCl$_2$, 0.75g NaHCO$_3$ and 4.21 g NaCl in 15 ml water to complete filling the pores. Spraying was carried out at ambient temperature while tumbling the support in a rotating evaporating dish. The coated support was allowed to stand for about l hour and dried using a hot air gun while tumbling to ensure that essentially all of the Pd and Au were converted to the corresponding carbonates. In accordance with the improvement of the invention, the impregnated support was calcined in a flowing stream of non-reducing gas (flow rate 200 ml/min; system pressure 70 psig) to decompose all or substantially all of the palladium and gold carbonates. The temperature of calcination ($T_c$), calcination time ($t_c$) and non-reducing gas were varied and are specified in Table I for each run.

At the end of the calcination period, the catalyst was reduced in a mixture of 20% H$_2$ and 80% N$_2$. If oxygen or air were employed as the non-reducing gas in the calcining step, the system was purged with N$_2$ to eliminate all traces of oxygen before introducing the H$_2$/N$_2$ mixture. In those instances where the temperatures of calcination and reduction are different, the catalyst was maintained in a nitrogen atmosphere until the temperature to be used for reduction was reached. The flow rate of the H$_2$/N$_2$ mixture was 500 ml/min and the system pressure was 70 psig. The temperature of reduction ($T_R$) and time of reduction ($t_R$) were varied in the runs and are set forth in Table I. When the reduction was complete, i.e., essentially all of the Pd and Au reduced to the metallic state, the catalyst was cooled under a N$_2$ stream and washed overnight with warm deionized water. The catalyst was dried and then activated by immersing for about 2 hours in an aqueous solution containing 5 wt.% potassium acetate and 0.5 wt. % potassium hydroxide. After drying, the catalysts were evaluated for their ability to produce vinyl acetate using Procedure A at a pressure of 35 psig, a temperature of 132° C. and space velocity of 455/hr. The results are set forth in Table I.

Figure 1:
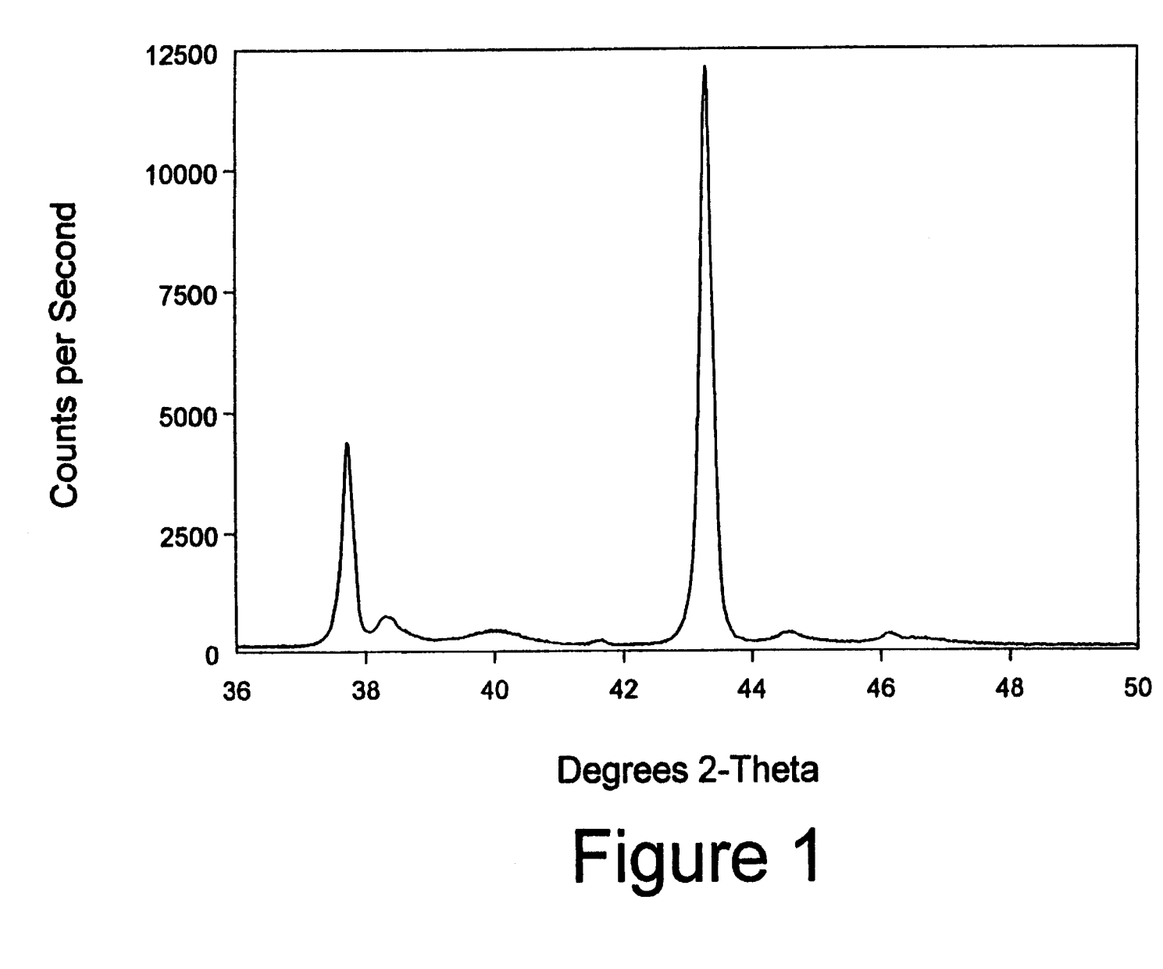
FIG. 1 is the X-ray diffraction profile of the high selectivity palladium-gold catalyst of Example 1A showing the peaks centered at about 38.30 and 40.0° 2-Theta corresponding to gold-enriched and palladium-enriched crystallites, respectively.

All of the Pd—Au catalysts prepared in accordance with the above-described procedure, which incorporates high temperature calcination prior to reduction with hydrogen, had segregated palladium-enriched and gold-enriched crystallite phases appearing as two distinct peaks in the x-ray diffraction pattern between the 2-Theta angles of 38° and 41°. For the purpose of this invention, the terms palladium-enriched and gold-enriched are understood to be based on the metal stoichiometry. FIG. 1 is the x-ray diffraction profile obtained for the Pd—Au catalyst of Example 1A and is representative of the x-ray diffraction patterns obtained for all of the catalysts obtained when the hydrogen reduction is conducted above about 350° C. and which typically exhibit improved selectivity. The peaks centered at about 38.30 and 39.9° 2-Theta correspond to the palladium-enriched and gold-enriched crystallites with d-space separations of the Miller 111 index plane of 2.354 Å and 2.258 Å, respectively.

TABLE I

| | 1A | 1B* | 1C* | 1D* | 1E* | 1F* | 1G* | 1H* | 1I* |
|---|---|---|---|---|---|---|---|---|---|
| Non-reducing gas | air | air | air | air | air | air | air | N$_2$ | N$_2$ |
| $T_c$ (° C.) | 500 | 500 | 500 | 500 | 500 | 300 | 400 | 425 | 500 |
| $t_c$ (hrs) | 3 | 3 | 3 | 3 | 3 | 3 | 3 | 3 | 3 |
| $T_R$ (° C.) | 500 | 500 | 500 | 500 | 350 | 500 | 425 | 425 | 500 |
| $t_R$ (hrs) | 3 | 3 | 3 | 3 | 3 | 3 | 3 | 3 | 3 |
| % Pd | 1.19 | 1.22 | N.D. | 1.17 | 1.22 | 1.21 | 1.31 | 1.17 | 1.17 |
| % Au | 0.53 | 0.55 | N.D. | 0.53 | 0.55 | 0.55 | 0.59 | 0.53 | 0.53 |
| Oxygen Conversion (%) | 98.2 | 98.0 | 97.9 | 97.7 | 97.6 | 99.2 | 98.4 | 99.3 | 98.3 |
| Percent Selectivity | 70.4 | 70.1 | 69.4 | 70.7 | 67.6 | 69.2 | 67.8 | 67.1 | 68.2 |
| Percent Yield | 69.2 | 68.7 | 68.0 | 69.0 | 66.0 | 68.7 | 66.7 | 66.7 | 67.1 |

*Two applications of Na$_2$CO$_3$ solution were made with metal salts' deposition and drying between applications. 1.75 N Na$_2$CO$_3$ solution was used for B, E, F, H and I. 1.25 N Na$_2$CO$_3$ solution was used for D. 1.5 N Na$_2$CO$_3$ solution was used for G.

EXAMPLE 2

To demonstrate the versatility of the improved Pd—Au catalysts obtained by the process of the invention, a catalyst produced in accordance with the procedure of Example 1A was evaluated for the production of vinyl acetate using different reaction conditions. Feed ratios used were the same as for Procedure A. Reaction conditions and results obtained are provided in Table II. Percent selectivity and yield are based on oxygen and space-time-yield is reported as grams of vinyl acetate produced per liter of catalyst per hour (g VA/l cat-hr).

TABLE II

|  | 2A | 2B | 2C | 2D | 2F |
|---|---|---|---|---|---|
| Reaction Temperature (° C.) | 132 | 140 | 140 | 150 | 160 |
| Reaction Pressure (psig) | 35 | 35 | 45 | 45 | 45 |
| Space Velocity (/hr) | 455 | 641 | 641 | 850 | 1,000 |
| Oxygen Conversion (%) | 97.1 | 88.1 | 89.2 | 83.6 | 85.2 |
| Percent Selectivity | 70.2 | 70.6 | 71.1 | 67.1 | 60.4 |
| Percent Yield | 68.2 | 62.3 | 63.4 | 56.1 | 51.6 |
| Space-Time-Yield | 174 | 235 | 239 | 280 | 303 |

EXAMPLE 3

Catalysts having varying levels of palladium and gold were prepared following the general procedure of Example I except that 0.81 N aqueous $Na_2CO_3$ was employed to treat the alumina. Also, after treatment with the aqueous solution containing the palladium and gold salts and partial drying, the impregnated support was treated a second time with 0.81 N aqueous $Na_2CO_3$ before drying. All other treatments were identical to that of Example 1A, including the calcining and reduction steps. The palladium and gold weight loadings, loading ratios as well as the weight percentages of palladium and gold in the final catalyst are given in Table III. The catalysts were evaluated for vinyl acetate productivity using Procedure A and reaction conditions and results are reported in Table III.

TABLE III

|  | 3A | 3B | 3C | 3D |
|---|---|---|---|---|
| Pd Loading (wt.%) | 1.2 | 0.6 | 0.6 | 0.9 |
| Au Loading (wt. %) | 0.3 | 0.6 | 0.3 | 0.45 |
| Wt. Loading Ratio (Pd:Au) | 4:1 | 1:1 | 2:1 | 2:1 |
| Pd Wt. % (actual) | 1.28 | 0.6 | 0.73 | 0.89 |
| Au Wt. % (actual) | 0.3 | 0.55 | 0.33 | 0.39 |
| Reaction Temperature (° C.) | 132 | 132 | 132 | 132 |
| Reaction Pressure (psig) | 35 | 35 | 35 | 35 |
| Space Velocity (/hr.) | 455 | 455 | 455 | 455 |
| Oxygen Conversion (%) | 99.2 | 90.7 | 87.4 | 97.1 |
| Percent Selectivity | 64.3 | 67.7 | 68.7 | 64.2 |
| Percent Yield | 63.8 | 61.4 | 60.8 | 62.3 |

EXAMPLE 4

To demonstrate the ability to vary the base used for the impregnation, Example 1A was repeated except that 1.25N NaOH was substituted for the sodium carbonate and after contacting with the palladium and gold salts solution, a second contacting with 1.25 N aqueous NaOH was made. Also, the calcining temperature was 200° C. and the reduction was carried out at 350° C. All other procedures were as described for Example 1A. The Pd—Au catalyst (1.11% Pd; 0.49% Au) was evaluated for the production of vinyl acetate using Procedure A (temperature 132° C.; pressure 35 psig; space velocity 455/hr). Oxygen conversion was 95.1% and percent selectivity and percent yield (based on oxygen) were 66.9 and 63.6, respectively.

EXAMPLE 5

The following experiment was conducted to demonstrate the ability to produce a catalyst having enhanced activity by varying the preparation procedure, namely, the conditions employed for the calcination and reduction. Palladium and gold were deposited on alumina as described in Example I and the impregnated support was calcined in a flowing stream of air (flow rate 200 ml/min; system pressure 70 psig) for one hour at 200° C. to decompose approximately 40% of the Pd and Au carbonates. The system was then purged with nitrogen to eliminate all traces of oxygen. A mixture of 20% hydrogen and 80% nitrogen was introduced (flow rate 500 ml/min; system pressure 70 psig) and the temperature increased to 500° C. at a rate of about 10° C. per minute and maintained for one hour to complete the reduction. The catalyst was recovered and activated following the same procedure as employed in Example I and evaluated using Procedure B. The catalyst contained 1.16% palladium and 0.49% gold and exhibited significantly improved activity compared to the catalyst of Example 1. Reaction conditions employed for the catalyst evaluation and results obtained are provided in Table IV.

TABLE IV

|  | 5A | 5B | 5C | 5D |
|---|---|---|---|---|
| Reaction Temperature (° C.) | 130 | 135 | 140 | 150 |
| Reaction Pressure (psig) | 35 | 35 | 35 | 110 |
| Space Velocity (/hr) | 3800* | 3800* | 3800* | 3800* |
| Oxygen Conversion (%) | 36.8 | 42.3 | 49.6 | 73.5 |
| Percent Selectivity | 75.3 | 73.2 | 70.8 | 64.4 |
| Percent Yield | 27.7 | 31.0 | 35.1 | 47.3 |
| Space-Time-Yield | 597 | 671 | 754 | 1072 |

*To obtain this space velocity, 10 ml catalyst was diluted to 33 ml total volume with inert alumina.

The above data demonstrate the ability to vary productivity (space-time-yeild) by varying reaction conditions. It is particularly noteworthy that for 5D it was possible to achieve space-time-yields greater than 1000 gVA/l cat-hr under the reported conditions.

EXAMPLE 6

To illustrate the different characteristics of catalysts obtained using different calcination and reduction conditions, catalysts prepared following the procedure of Examples 1 and 5 were evaluated for the production of vinyl acetate under conditions of high oxygen conversion (Procedure A) and high space velocity (Procedure B) and the results are tabulated in Table V.

TABLE V

| Catalyst of Example | 1 | 5 | 1 | 5 |
|---|---|---|---|---|
| Procedure Used to Evaluate | A | A | B | B |
| Reaction Temperature (° C.) | 132 | 132 | 150 | 150 |
| Reaction Pressure (psig) | 35 | 35 | 35 | 35 |
| Space Velocity (/hr) | 455 | 455 | 1,350 | 1,350 |
| Oxygen Conversion (%) | 97.3 | 100 | 71.9 | 83.1 |
| Percent Selectivity | 70.8 | 64.6 | 67.9 | 69.7 |
| Percent Yield | 68.9 | 64.6 | 48.8 | 57.9 |
| Space-Time-Yield | 175 | 164 | 373 | 442 |

EXAMPLE 7

A Pd—Au catalyst was prepared following the general procedure of Example 5 using titania ($TiO_2$) as the support. The titania used had a surface area of $4m^2/g$, pore volume of 24 ml/g and crush strength of 15–20 lbs. Deposition of the palladium and gold salts was accomplished following the same procedure as used for Example IA except that 100 g of the support was used and the volumes of reagents were correspondingly reduced. The impregnated support was calcined at 200° C. in oxygen (flow rate 50 ml/min; atmospheric pressure) for one hour. At the completion of the calcining operation, the system was purged with helium for 30 minutes and a mixture of 5% $H_2$/95% $N_2$ introduced. The temperature was then raised to 500° C. at a rate of about 10° C./minute and maintained at 500° C. for one hour to complete the reduction. Atmospheric pressure was maintained during the purging and reduction operations. The catalyst was washed and activated per the standard procedure and evaluated for production of vinyl acetate using the same conditions as in Example 2. The catalyst contained 1.03 wt % Pd and 0.43% Au. Results obtained are set forth in Table VI. Percent selectivity and yield are based on oxygen.

TABLE VI

|  | 7A | 7B | 7C | 7D | 7F |
|---|---|---|---|---|---|
| Reaction Temperature (C.) | 132 | 140 | 140 | 150 | 160 |
| Reaction Pressure (psig) | 35 | 35 | 45 | 45 | 45 |
| Space Velocity (/hr) | 455 | 641 | 641 | 850 | 1,000 |
| Oxygen Conversion (%) | 98.2 | 86.8 | 84.6 | 80 | 82.2 |
| Percent Selectivity | 67.3 | 70.5 | 69.7 | 70.5 | 67.8 |
| Percent Yield | 66.1 | 61.2 | 58.9 | 56.4 | 55.7 |
| Space-Time-Yield | 168 | 230 | 222 | 282 | 330 |

EXAMPLE 8

Alumina supported Pd—Au catalysts were prepared using different calcination and reduction conditions to show the effect on catalyst activity. All of the catalysts were evaluated using the micro scale procedure, and the rate of vinyl acetate production was determined. Calcination and reduction conditions, weight percentages of palladium and gold, and rates of reaction for each of the catalysts, identified as 8A–J, are set forth in the Table VII.

Figure 2:
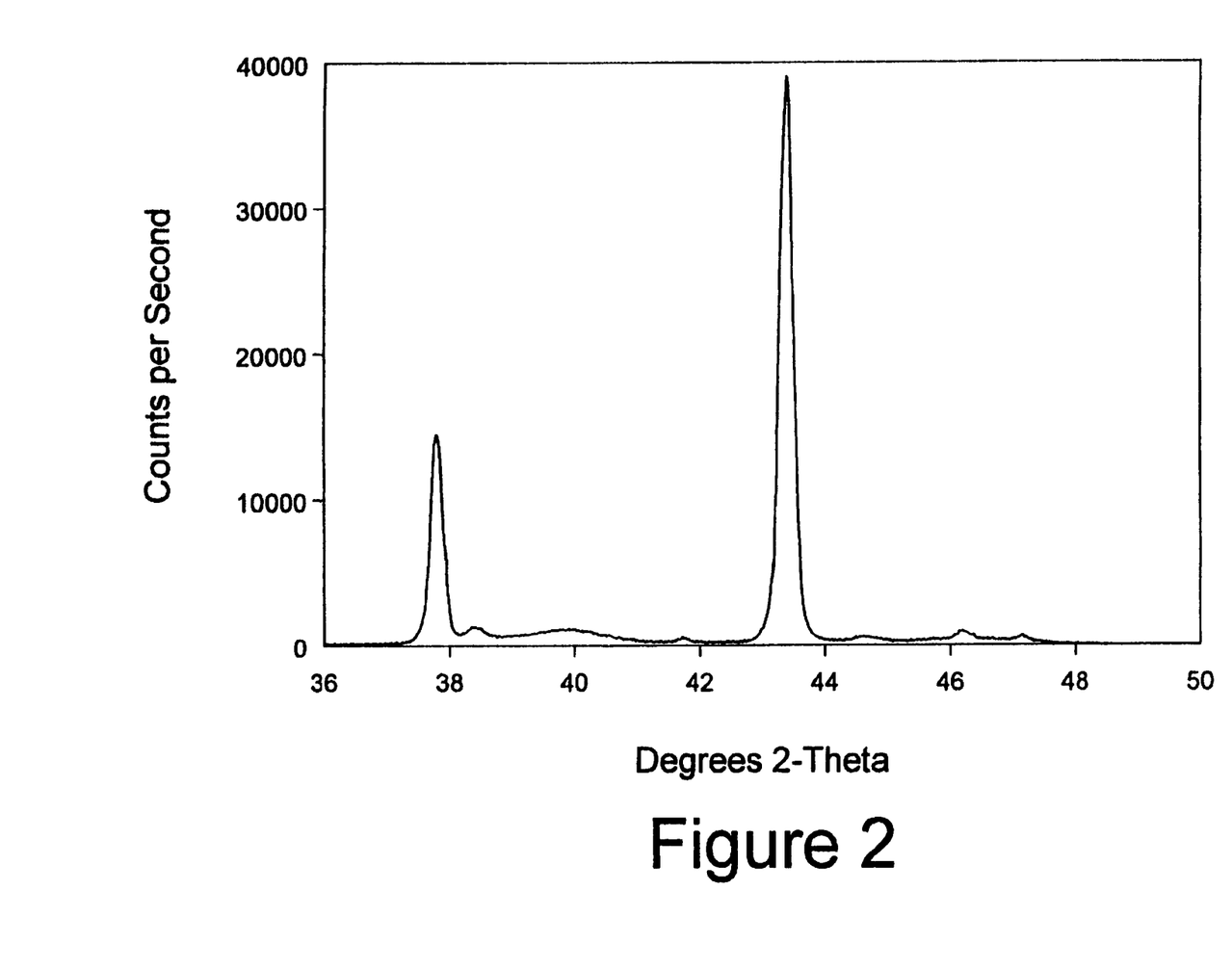
FIG. 2 is the x-ray diffraction profile of the high activity palladium-gold catalyst of Example 8E showing the peaks centered at about 38.3° to 39.8° 2-Theta which correspond to the gold and palladium crystallites, respectively.

Catalyst 8E was examined by x-ray diffraction and FIG. 2 is the x-ray diffraction profile for the catalyst. The peaks centered at about 39.8° and about 38.3° 2-Theta, respectively, correspond to the palladium and gold crystallites with d-space separations of the Miller 11 index plane of 2.265 Å and 2.348 Å, respectively.

catalysts were prepared and compared for the micro scale production of vinyl acetate. All of the catalysts used the same impregnated support which was obtained following the procedure of Example 1. The first catalyst (Example 10) was prepared in accordance with the invention by calcining the impregnated support at 200° C. in oxygen and then reducing at 500° C. following the procedure of Example 5. A second catalyst (Example 11) was prepared in accordance with the invention by calcining at 200° C. before reducing with alkaline formaldehyde—a conventional reduction procedure used in the prior art. For the alkaline formaldehyde treatment, 200 grams catalyst were saturated with about 65 ml of a solution comprised of 24 ml of 37 percent formaldehyde solution and 56 ml of 0.81 N sodium hydroxide. After standing at room temperature for 15 minutes, the sample was heated to 66° C. and held for 30 minutes. The mixture was cooled to room temperature and washed by decantation with 5 weight percent acetic acid followed by a continuous overnight wash with warm deionized water and drying at 105° C. in air. The third catalyst (Comparative Example A) omitted the calcining step and the reduction was identical to that employed for the catalyst of Example 10. The fourth catalyst (Comparative Example B) was not calcined before reducing the metal salts using alkaline formaldehyde. The fifth catalyst (Comparative Example C) was prepared by oxidizing and reducing a portion of the virgin catalyst of Comparative Example B in accordance with the procedure of U.S. Pat. No. 5,194,417. Each of the five catalysts was activated by treating with potassium acetate as described in Example 1 and evaluated in the micro scale reaction to determine catalyst activity. Reaction rates were as follow:

CATALYST OF EXAMPLE 10—0.647 $\mu$mol/g cat.-sec
CATALYST OF EXAMPLE 11—0.396 $\mu$mol/g cat.-sec
CATALYST OF COMPARATIVE EXAMPLE A—0.456 $\mu$mol/g cat.-sec
CATALYST OF COMPARATIVE EXAMPLE B—0.309 $\mu$mol/g cat.-sec
CATALYST OF COMPARIATIVE EXAMPLE C—0.270 $\mu$mol/g cat.-sec

TABLE VII

|  | 8A | 8B | 8C | 8D | 8E[1] | 8F | 8G[2] | 8H | 8I | 8J |
|---|---|---|---|---|---|---|---|---|---|---|
| Non-reducing gas | $O_2$ | $O_2$ | $O_2$ | $O_2$ | $O_2$ | $O_2$ | $O_2$ | $O_2$ | $O_2$ | $O_2$ |
| $T_x$ (° C.) | 130 | 170 | 200 | 200 | 200 | 350 | 350 | 350 | 500 | 500 |
| $t_c$ (hrs) | 1 | 1 | 1 | 1 | 1 | 1 | 1 | 1 | 1 | 1 |
| $T_R$ (° C.) | 500 | 500 | 100 | 300 | 500 | 100 | 300 | 500 | 100 | 300 |
| $t_R$ (hrs) | 1 | 1 | 1 | 1 | 1 | 1 | 1 | 1 | 1 | 1 |
| % Pd | 1.11 | 1.11 | 1.16 | 1.11 | 1.16 | 1.11 | 1.11 | 1.11 | 1.16 | 1.11 |
| % Au | 0.48 | 0.48 | 0.49 | 0.48 | 0.49 | 0.48 | 0.48 | 0.48 | 0.49 | 0.48 |
| Reaction Rate $\mu$mol/g · cat-sec) | 0.593 | 0.515 | 0.613 | 0.687 | 0.791 | 0.472 | 0.535 | 0.688 | 0.354 | 0.305 |

[1]Reaction rate data is the average of five (5) runs.
[2]Reaction rate data is the average of two (2) runs.

EXAMPLE 9

A supported palladium-gold catalyst was prepared following the procedure of Example 5 except that the calcination was conducted using a helium atmosphere and 5% $H_2$/95% $N_2$ for the reduction. After reaching 500° C., the temperature was maintained for 1 hour. Catalyst activity was determined using the micro scale procedure and the rate of reaction was 0.601 $\mu$mol/g cat.-sec.

EXAMPLES 10 AND 11
COMPARATIVE EXAMPLES A–C

To demonstrate the improved results obtained by calcining before reducing the palladium and gold salts, five It is apparent from the above data that the reaction rates obtained with the catalyst of the invention (Examples 10 and 11), which includes a calcining step before reduction, are significantly higher than obtained with the respective identically prepared catalyst except for omission of the calcining step (Comparative Examples A and B). Also, the data shows that when a similar treatment is used after reduction, such as for the catalyst of Comparative Example C, improved reaction rates are not obtained.

EXAMPLE 12

To demonstrate the ability to vary the method by which the supports are impregnated with the palladium and gold, the following experiment was conducted. For this example, 300 g alumina (⁵⁄₁₆" pellet; 98% alpha alumina; pore volume 0.23 ml/g; surface area approximately 4 m²/g) were sprayed with 50 ml of an aqueous solution containing 6.503 g $PdCl_2$, 3.288 g $HAuCl_4$, 4.203 g NaCl and 0.752 g $NaHCO_3$ in a rotating dish. The mixture was allowed to stand for 30 minutes, and the water then removed by heating with a heat gun. The support was then treated with 75 ml 2.33 N aqueous solution of $Na_2CO_3$ and dried. The impregnated support thus obtained was calcined at 200° C. in oxygen for 1 hour. After purging to remove oxygen, the catalyst was reduced by introducing a 5 percent hydrogen/95 percent nitrogen mixture and increasing the temperature to 500° C. over a period of about 1 hour and then maintaining at 500° C. and atmospheric pressure for an additional hour. When activated in the usual manner and evaluated in the micro reactor for the production of vinyl acetate, the catalyst gave a reaction rate of 0.599 μmol/g cat.-sec.

EXAMPLE 13

To demonstrate the ability to impregnate the support using sodium metasilicate, the procedure of Example 1 was repeated except that the sodium carbonate solution was replaced with a 2.33 N sodium metasilicate solution. The impregnated support was calcined and reduced as described in Example 12 to provide a Pd—Au supported catalyst which, after activation with potassium acetate and potassium hydroxide, had a reaction rate of 0.559 μmol/g cat.-sec for the production of vinyl acetate in the micro reactor.

EXAMPLE 14 AND COMPARATIVE EXAMPLES D and E

Three high activity Pd—Au catalysts supported on silica-alumina and referred to as 14A, 14B and 14C were prepared. Catalyst 14A was prepared by impregnating 100 g silica-alumina support (5mm, spheres; approximately 5% alumina; pore volume 0.62 ml/g; surface area 140 m²/g; bulk density 0.77 g/ml, with a solution consisting of 1.02 g $HAuCl_4$, 2.11 g $PdCl_2$, 0.25 g $NaHCO_3$ and 1.40 g NaCl in 62 ml water. The support was then immersed in approximately 100 ml of 1.05 N aqueous sodium carbonate and allowed to stand for about 16 hours. After removing the water by decantation, the impregnated support was dried in a convection oven at 105° C.

Five grams of the support impregnated in the above manner were then calcined by heating at 230° C. for 1 hour in a flowing stream of oxygen (flow rate 50 m/min; atmospheric pressure) to decompose approximately 45% of the palladium and gold carbonates. The system was then purged with helium to remove all traces of oxygen and a mixture of 5% hydrogen and 95% nitrogen introduced at the same flow rate and pressure. The temperature was raised to 500° C. at a rate of 10° C. per minute and maintained at 500° C. for 1 hour. After washing with deionized water and drying, the catalyst was activated by immersing for approximately 40 minutes in an aqueous solution containing 2.5 wt.% potassium acetate and drying. The catalyst contained 1.16 wt.% Pd and 0.39 wt. % Au.

Catalysts 14B and 14C were prepared identically except that the palladium and gold loadings were varied by changing the concentration of metal salts in the first aqueous solution used to treat the silica-alumina support. Catalyst 14B contained 1.17 wt. % Pd and 0.75 wt. % Au and Catalyst 14C contained 2.21 wt. % Pd and 0.75 wt. % Au.

Additionally for comparison, two catalysts were prepared, identified as Comparative Catalysts D and E. Comparative Catalyst D was prepared identically to Catalyst 14A except that 1.0 N aqueous sodium carbonate was employed during the deposition, the catalyst was not calcined and the reducing agent was hydrazine. Comparative Catalyst E was also prepared identically to Catalyst 14A except that 1.0 N aqueous $Na_2SiO_3$ was used in place of the aqueous sodium carbonate and the catalyst was not calcined before reducing with hydrazine. The hydrazine reductions were accomplished by covering the catalyst pellets with a 35% aqueous solution of hydrazine and allowing to stand for 6 hours under ambient conditions.

All of the above catalysts, i.e., 14A, B and C, and comparative catalysts D and E were evaluated using the micro scale reaction to determine the rate of vinyl acetate formation. All of the catalysts were activated with potassium acetate as described for 14A before being evaluated. Results were as follow:

| | |
|---|---|
| Catalyst 14A | 0.848 μmol/g cat.-sec |
| Catalyst 14B | 1.06 μmol/g cat.-sec |
| Catalyst 14C | 0.943 μmol/g cat.-sec |
| Comparative Catalyst D | 0.464 μmol/g cat.-sec |
| Comparative Catalyst E | 0.592 μmol/g cat.-sec |

Figure 3:
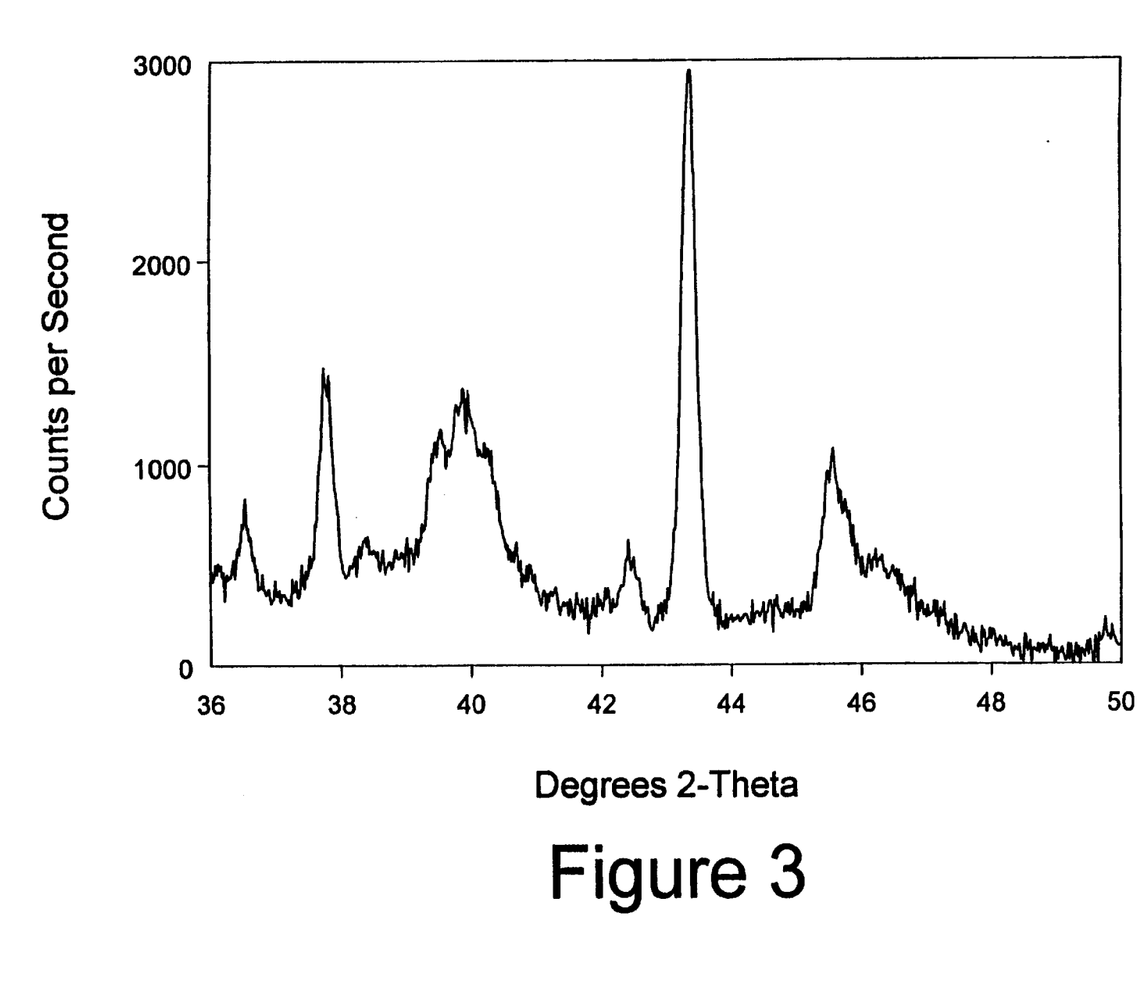
FIG. 3 is the x-ray diffraction profile of the high activity palladium-gold catalyst of Example 14A showing the peaks centered at about 38.3° to 39.8° 2-Theta corresponding to the gold and palladium crystallites, respectively.

Catalyst 14A was examined by x-ray diffraction and FIG. 3 is the x-ray diffraction profile for the catalyst. The peaks centered at about 39.8° and about 38.2° 2-Theta correspond to the palladium and gold crystallites with d-space separations of the Miller 111 index plane of 2.265 Å and 2.353 Å, respectively.

We claim:

1. In a process for the preparation of a supported palladium-gold catalyst wherein an inert support is impregnated with palladium and gold salts and the salts subsequently reduced to the corresponding metals, to produce catalysts having increased selectivity and activity for the vapor phase production of vinyl acetate by the reaction of ethylene, acetic acid and oxygen, the improvement comprising calcining the impregnated support having the palladium and gold salts deposited thereon by heating in a non-reducing atmosphere at a temperature from about 100° C. to about 600° C. to effect decomposition of at least 10 percent of the palladium and gold salts before reducing the palladium and gold to the metallic state.

2. The process of claim 1 wherein the supported palladium-gold catalyst contains from 0.1 to 3 weight percent palladium, from 0.1 to 3 weight percent gold and the weight ratio of palladium to gold is from 5:1 to 1:3.

3. The process of claim 2 wherein the inert support has a pore volume from 0.1 to 0.75 cc/g and surface area is from 0.5 to 500 m²/g.

4. The process of claim 3 wherein the inert support is selected from the group consisting of alumina, silica, silica-alumina and titania, the catalyst contains 0.5 to 1.5 weight percent palladium and 0.25 to 0.75 weight percent gold and the weight ratio of palladium to gold is from 2.5:1 to 1:1.5.

5. The process of claim 4 wherein the inert support has a pore volume from 0.2 to 0.65 cc/g and surface area from 1 to 200 m²/g.

6. The process of claim 5 wherein the inert support is alumina having a surface area from 2 to 50 m²/g and alpha-alumina content greater than 95 percent.

7. The process of claim 5 wherein the inert support is silica or silica-alumina having a surface area from 30 to 200 m²/g.

8. The process of claim 1 wherein the non-reducing atmosphere is an inert or oxidizing gas selected from the group consisting of helium, nitrogen, argon, neon, nitrogen oxides, oxygen, air and carbon dioxide.

9. The process of claim 8 wherein the palladium and gold are reduced at a temperature from ambient to 550° C. and the reducing agent is selected from the group consisting of ammonia, carbon monoxide, hydrogen, hydrocarbons, olefins, aldehydes, alcohols, hydrazine, primary amines, carboxylic acids, carboxylic acid salts and carboxylic acid esters.

10. The process of claim 9 wherein the impregnated support is calcined at a temperature from 350 to 600° C. and 70 percent or more of the palladium and gold salts are decomposed.

11. The process of claim 10 wherein the reducing agent is hydrogen or a mixture of hydrogen with an inert gas and the temperature of reduction is 100 to 550° C.

12. The process of claim 11 wherein the impregnated support is calcined at 400 to 550° C.

13. The process of claim 12 wherein the temperature of reduction is 350 to 525° C.

14. The process of claim 9 wherein the impregnated support is calcined at a temperature up to 350° C. and 10 to 70 percent of the palladium and gold salts are decomposed.

15. The process of claim 14 wherein the reducing agent is hydrogen or a mixture of hydrogen and an inert gas and the temperature of reduction is 100 to 550° C.

16. The process of claim 15 wherein the temperature of reduction is 150 to 525° C.

17. The process of claim 15 wherein the impregnated support is calcined at 150 to 275° C. and reduced while increasing the temperature from 150 to 275° C. up to 475 to 525° C. at a rate of 0.1 to 25° C. per minute.

18. A process for the production of a supported palladium-gold catalyst containing from 0.1 to 3 weight percent palladium, 0.1 to 3 weight percent gold and having a weight ratio of palladium to gold from 5:1 to 1:3 comprising:
(1) impregnating an inert support selected from the group consisting of alumina and titania and having a pore volume from 0.1 to 0.75 cc/g and surface area from 0.5 to 500 $m^2/g$ with palladium and gold salts by contacting said support with an aqueous solution of an alkali metal hydroxide, alkali metal carbonate, alkali metal bicarbonate or alkali metal metasilicate to fill from 25 to 95 percent of the absorptive capacity of the support and thereafter with an aqueous solution of tetrachloroauric acid and palladium chloride or sodium chloropalladite to effect essentially complete precipitation of the palladium and gold salts;
(2) drying to remove water;
(3) calcining by heating in an inert or oxidizing gas selected from the group consisting of helium, nitrogen, argon, neon, nitrogen oxides, oxygen, air and carbon dioxide at a temperature from 100 to 350° C. to decompose from 10 to 70 percent of the palladium and gold salts; and
(4) reducing in hydrogen or a mixture of hydrogen and an inert gas at a temperature from 100 to 550° C. to convert the palladium and gold to the metallic state.

19. The process of claim 18 wherein the calcination is conducted at a temperature from 150 to 275° C. and the reduction is carried out while increasing the temperature from 150 to 275° C. up to 475 to 525° C. at a rate of 0.1 to 25° C. per minute.

20. The process of claim 18 wherein the catalyst is activated by treating with 1 to 15 weight percent solution of an alkali metal carboxylate, alkali metal hydroxide or mixture thereof.

21. The process of claim 20 wherein the catalyst is activated by treating with an aqueous solution containing 1 to 15 weight percent potassium acetate and up to 5 weight percent potassium hydroxide.

22. The process for the production of a supported palladium-gold catalyst containing from 0.1 to 3 weight percent palladium and 0.1 to 3 weight percent gold and having a weight ratio of palladium to gold from 5:1 to 1:3 comprising:
(1) impregnating an inert support selected from the group consisting of silica and silica-alumina and having a pore volume from 0.1 to 0.75 cc/g and surface area from 0.5 to 500 $m^2/g$ with palladium and gold salts by contacting said support with an aqueous solution of tetrachloroauric acid and palladium chloride or sodium chloropalladite to essentially completely fill the absorptive capacity of the support and thereafter with an aqueous solution of an alkali metal carbonate to effect essentially complete precipitation of the palladium and gold salts;
(2) drying to remove water;
(3) calcining by heating in an inert or oxidizing gas selected from the group consisting of helium, nitrogen, argon, neon, nitrogen oxides, oxygen, air and carbon dioxide at a temperature from 100 to 350° C. to decompose from 10 to 70 percent of the palladium and gold salts; and
(4) reducing in hydrogen or a mixture of hydrogen and an inert gas at a temperature from 100 to 550° C. to convert the palladium and gold to the metallic state.

23. The process of claim 22 wherein the calcination is conducted at a temperature from 150 to 275° C. and the reduction is carried out while increasing the temperature from 150 to 275° C. up to 475 to 525° C. at a rate of 0.1 to 25° C. per minute.

24. The process of claim 22 wherein the catalyst is activated by treating with 1 to 15 weight percent solution of an alkali metal carboxylate.

25. The process of claim 24 wherein the catalyst is activated by treating with an aqueous solution containing 1 to 4 weight percent potassium acetate.

26. A process for the production of a supported palladium-gold catalyst containing from 0.1 to 3 weight percent palladium, 0.1 to 3 weight percent gold and having a weight ratio of palladium to gold from 5:1 to 1:3 comprising:
(1) impregnating an inert support selected from the group consisting of alumina, silica, silica-alumina and titania and having a pore volume from 0.1 to 0.75 cc/g and surface area from 0.5 to 500 $m^2/g$ with palladium and gold salts by contacting said support with an aqueous solution of an alkali metal hydroxide, alkali metal carbonate, alkali metal bicarbonate or alkali metal metasilicate to fill from 25 to 95 percent of the absorptive capacity of the support and thereafter with an aqueous solution of tetrachloroauric acid and palladium chloride or sodium chloropalladite to effect essentially complete precipitation of the palladium and gold salts;
(2) drying to remove substantially all associated water;
(3) calcining by heating in an inert or oxidizing gas selected from the group consisting of helium, nitrogen, argon, neon, nitrogen oxides, oxygen, air and carbon dioxide at a temperature from 350 to 600° C. to decompose 70 percent or more of the palladium and gold salts; and
(4) reducing in hydrogen or a mixture of hydrogen and an inert gas at a temperature from 100 to 550° C. to convert the palladium and gold to the metallic state.

27. The process of claim 26 wherein the impregnated support is calcined at a temperature from 400 to 550° C. and reduced at a temperature from 350 to 525° C.

28. The process of claim 26 wherein the catalyst is activated by treating with 1 to 15 weight percent solution of an alkali metal carboxylate, alkali metal hydroxide or mixture thereof.

29. A supported palladium-gold catalyst obtained by the process of any one of the preceding claims.

* * * * *

UNITED STATES PATENT AND TRADEMARK OFFICE
CERTIFICATE OF CORRECTION

PATENT NO. : 6,022,823
DATED : February 8, 2000
INVENTOR(S) : Millennium Petrochemicals, Inc.

It is certified that error appears in the above-identified patent and that said Letters Patent is hereby corrected as shown below:

Column 2, line 65 reads "38.30" and should read -- 38.3° --.

Column 3, line 52 reads "porous carried" and should read -- porous carrier --.

Column 5, line 15 reads "thereof Calcination" and should read -- thereof. Calcination Column 5, line 25 reads "0.23 mug;" and should read -- 0.23ml/g; --.

Column 9, line 34 reads "about I hour" and should read -- about 1 hour --.

Column 10, line 32 reads "38.30" and should read -- 38.3° --.

Column 12, line 30 reads "SD" and should read -- 5D --.

Column 12, line 65 reads "50 ml/min" and should read -- 50ml/min --.

Column 13, line 38 reads "Miller 11" and should read -- Miller 111 --.

UNITED STATES PATENT AND TRADEMARK OFFICE
CERTIFICATE OF CORRECTION

PATENT NO. : 6,022,823
DATED : February 8, 2000
INVENTOR(S) : Millennium Petrochemicals, Inc.

It is certified that error appears in the above-identified patent and that said Letters Patent is hereby corrected as shown below:

Column 15, line 48 reads "50m/min" and should read -- 50 ml/min. --.

Column 16, line 6 reads "Na2SiO$_3$," and should read -- Na$_2$SiO$_3$ --.

Signed and Sealed this

First Day of May, 2001

Attest:

NICHOLAS P. GODICI

Attesting Officer        Acting Director of the United States Patent and Trademark Office